United States Patent [19]
Dietz et al.

[11] Patent Number: 5,689,110
[45] Date of Patent: Nov. 18, 1997

[54] CALIBRATION METHOD AND APPARATUS FOR OPTICAL SCANNER

[75] Inventors: Louis J. Dietz; Thomas M. Baer, both of Mountain View, Calif.

[73] Assignee: Biometric Imaging, Inc., Mountain View, Calif.

[21] Appl. No.: 670,540

[22] Filed: Jun. 27, 1996

Related U.S. Application Data

[62] Division of Ser. No. 300,160, Sep. 2, 1994, abandoned.

[51] Int. Cl.$^6$ ............................................. G01J 3/443
[52] U.S. Cl. ............................ 250/252.1 A; 356/317
[58] Field of Search ................. 250/252.1 A, 252 R, 250/458.1, 459.1; 356/317

[56] References Cited

U.S. PATENT DOCUMENTS

| | | | |
|---|---|---|---|
| 2,850,239 | 9/1958 | Polanyi et al. | 235/92 |
| 3,790,492 | 2/1974 | Fulwyler | 252/301.1 R |
| 3,826,364 | 7/1974 | Bonner et al. | 209/3 |
| 3,854,050 | 12/1974 | Peterson et al. | 250/252.1 A |
| 3,900,265 | 8/1975 | Merlen et al. | 356/200 |
| 3,956,201 | 5/1976 | Seiner | 260/2.5 M |
| 3,973,129 | 8/1976 | Blumberg et al. | 250/461 B |
| 3,999,866 | 12/1976 | Mathisen | 356/246 |
| 4,035,085 | 7/1977 | Seiner | 356/179 |
| 4,150,295 | 4/1979 | Wieder | 250/458.1 |
| 4,249,826 | 2/1981 | Studievic et al. | 356/244 |
| 4,492,121 | 1/1985 | Lehto | 73/705 |
| 4,542,987 | 9/1985 | Hirschfeld | 356/44 |
| 4,599,901 | 7/1986 | Hirschfeld | 73/705 |
| 4,661,711 | 4/1987 | Harjunmaa | 356/243 |
| 4,683,579 | 7/1987 | Wardlaw | 377/11 |
| 4,741,043 | 4/1988 | Bacus | 382/6 |
| 4,845,552 | 7/1989 | Jaggi et al. | 358/93 |
| 4,979,824 | 12/1990 | Mathies et al. | 356/318 |

(List continued on next page.)

FOREIGN PATENT DOCUMENTS

| | | | |
|---|---|---|---|
| 0 266 881 | 5/1988 | European Pat. Off. | 21/64 |
| 1578478 A1 | 6/1987 | U.S.S.R. | |
| 1578478 | 7/1990 | U.S.S.R. | 250/252.1 A |

OTHER PUBLICATIONS

M.A. West, et al., "Practical standards for uv absorption and fluorescence spectrophotometry Developments in Photophysical Instrumentation Part 3," *American Laboratory* (Mar. 1977), vol. 9, No. 3; pp. 37–50.

E. A. Mroz, et al., "Fluorescence Analysis of Picoliter Samples", *Analytical Biochemistry* (1980), vol. 102, No. 1; pp. 90–96.

J. H. Tucker, et al., "Automated densitometry of cell pouplations in a continuous–notion imaging cell scanner", *Applied Optics* (1987), vol;. 26, No. 16; pp. 3315–3324.

(List continued on next page.)

*Primary Examiner*—David P. Porta
*Assistant Examiner*—Richard Hanig
*Attorney, Agent, or Firm*—Fulwider Patton Lee & Utecht

[57] ABSTRACT

A calibration method and device for a fluorescence spectrometer which uses fluorescence from a homogeneous solid state standard as the source of calibration fluorescence and wherein the solid state standard may be built into the optical scanner and the calibration may be automatically performed as a routine step when using the optical scanner. A gold standard establishes fluorescent units, and the fluorescence spectrometer is calibrated by reference to calibration standards, such as calibration rubies, which are themselves rated against the gold standard and built into the fluorescence spectrometer to provide an unchanging reference to the gold standard and by which simultaneous calibration of two or more channels of a multi-channel fluorescence spectrometer may be accomplished, including automatically calibrating a multi-channel optical scanner when it is turned on to achieve an acceptable level of sensitivity in each channel and to adjust for any relative shift in sensitivity between the channels.

15 Claims, 11 Drawing Sheets

U.S. PATENT DOCUMENTS

| | | | |
|---|---|---|---|
| 5,032,731 | 7/1991 | Dall'oglio | 250/458 |
| 5,073,498 | 12/1991 | Schwartz et al. | 436/8 |
| 5,084,394 | 1/1992 | Vogt et al. | 436/8 |
| 5,091,652 | 2/1992 | Mathies et al. | 250/458 |
| 5,107,422 | 4/1992 | Kamentsky et al. | 364/413.08 |
| 5,117,466 | 5/1992 | Buican et al. | 382/6 |
| 5,123,738 | 6/1992 | Yonemura | 356/243 |
| 5,205,291 | 4/1993 | Potter | 28/654 |
| 5,243,401 | 9/1993 | Sinya | 356/318 |
| 5,251,006 | 10/1993 | Honigs et al. | 356/319 |
| 5,274,240 | 12/1993 | Mathies et al. | 250/458.1 |
| 5,293,046 | 3/1994 | Wheatley | 250/458.1 |
| 5,315,993 | 5/1994 | Alcala | 128/634 |
| 5,459,677 | 10/1995 | Kowalski | 364/571.02 |
| 5,547,849 | 8/1996 | Baer et al. | 435/7.24 |
| 5,556,764 | 9/1996 | Sizto et al. | 435/7.24 |
| B1 4,741,043 | 8/1994 | Bacus | 382/6 |

OTHER PUBLICATIONS

A. Landay, et al., "Application of flow cytometry to the study of HIV infection", *AIDS* 1990, vol. 4, No. 5, pp. 479–497.

C. Wersig, et al., "Performance of commercial laser diodes in fluorimetric detection", *Advances in Fluorescence Sensing Technology* (1993), SPIE vol. 1885; pp. 389–400.

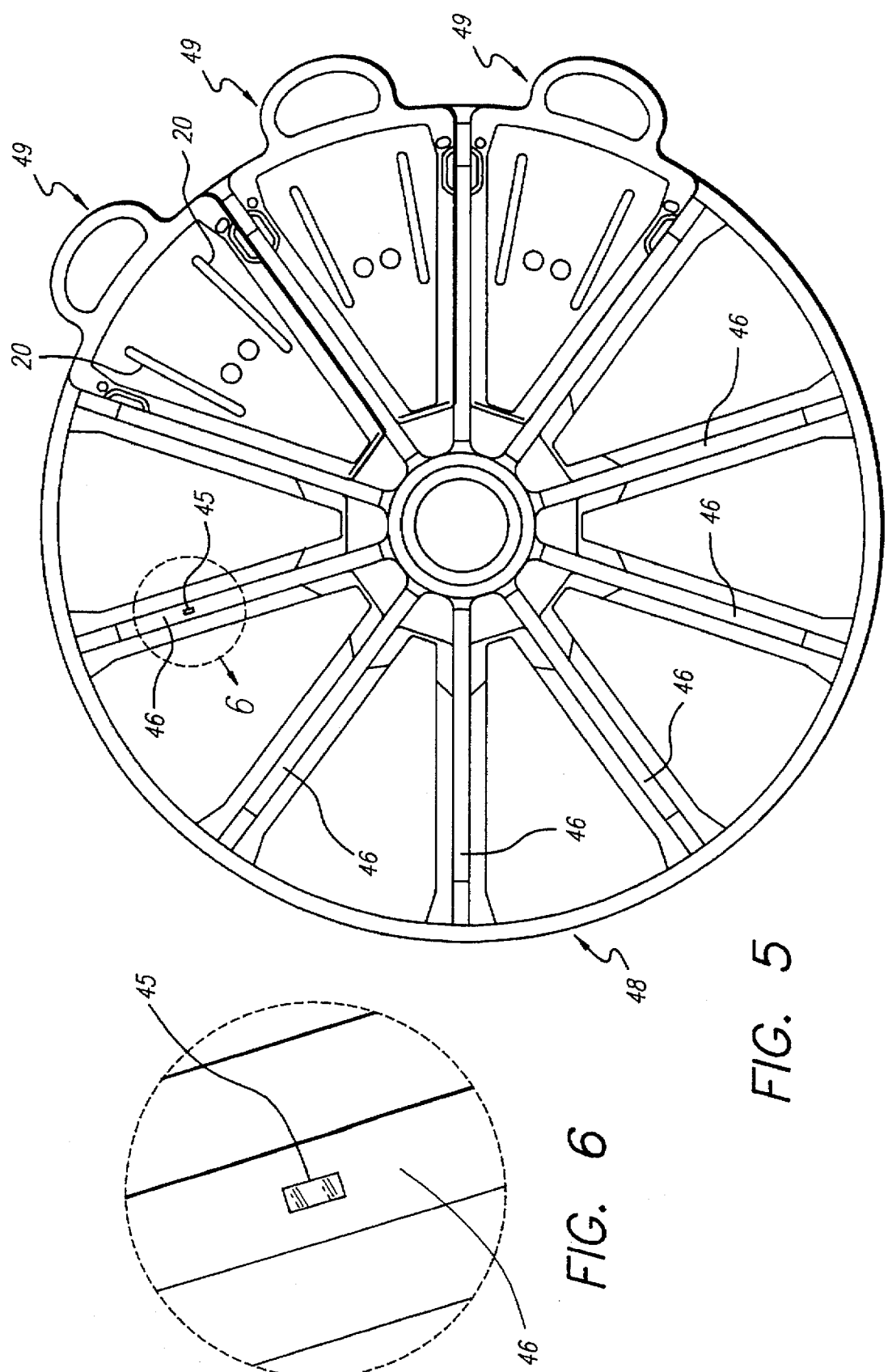

FIG. 9

| TEMPERATURE (C) | NORMALIZED INTENSITY |
|---|---|
| 5 | 0.71 |
| 6 | 0.72 |
| 7 | 0.74 |
| 8 | 0.75 |
| 9 | 0.76 |
| 10 | 0.78 |
| 11 | 0.80 |
| 12 | 0.82 |
| 13 | 0.84 |
| 14 | 0.86 |
| 15 | 0.88 |
| 16 | 0.89 |
| 17 | 0.90 |
| 18 | 0.92 |
| 19 | 0.93 |
| 20 | 0.94 |
| 21 | 0.95 |
| 22 | 0.97 |
| 23 | 0.98 |
| 24 | 0.99 |
| 25 | 1.00 |
| 26 | 1.01 |
| 27 | 1.02 |
| 28 | 1.04 |
| 29 | 1.05 |
| 30 | 1.06 |
| 31 | 1.08 |
| 32 | 1.09 |
| 33 | 1.11 |
| 34 | 1.12 |
| 35 | 1.14 |
| 36 | 1.16 |
| 37 | 1.17 |
| 38 | 1.19 |
| 39 | 1.20 |
| 40 | 1.22 |
| 41 | 1.23 |
| 42 | 1.25 |
| 43 | 1.27 |
| 44 | 1.28 |
| 45 | 1.30 |

CALIBRATION METHOD AND APPARATUS FOR OPTICAL SCANNER

This is a division of application Ser. No. 08/300,160, filed Sep. 2, 1994 now abandoned.

BACKGROUND OF THE INVENTION

This invention relates generally to a method and apparatus for calibrating a fluorescence spectrometer, hereafter also called an optical scanner or a scanner, for detecting fluorescence of particles in a liquid, and more particularly to improvements in a method and apparatus for calibrating an scanning optical imager.

It is often advantageous to analyze various samples, for example human blood samples, using optical scanning techniques. One such technique analyzes the fluorescence generated when a sample containing a substance such as an antibody labeled with a fluorescent dye, is excited by an excitation energy such as laser light. If the optical scanner is adequately sensitive and properly calibrated, the sample Can be analyzed for the presence and indeed the intensity of areas of increased fluorescent concentrations such as cells rich in the antigen to which the labeled antibody attaches.

In one such application using a scanning fluorescence imager a blood sample is mixed with an excess of different types of antibody, each type labeled with a fluorescent dye specific to that type of antibody. The antibodies have a specific affinity to certain target proteins characteristic of a particular type of cell found in the blood sample. The sample is placed in a capillary of known volume and then scanned with excitation radiation that causes the dye to fluoresce. The contents of the entire capillary are scanned, one small spot at a time, using a scanning system capable of detecting and quantifying the fluorescence generated. The fluorescence readings from each of the spots are then digitally processed to form a complete fluorescent image of the capillary. Since the antigens to which the antibodies attach are found in relatively high concentration in or on a certain type of cell, the fluorescently labeled antibodies are clustered in relatively high concentration in or on that type of cell. A relatively high concentration of fluorescence thus serves to identify that type of cell.

One system employing a fluorescence spectrometer is Flow Cytometery. Another capable of detecting fluorescence concentrations is disclosed in co-pending U.S. patent application Ser. No. 08/236,342 entitled "Apparatus and Method for Volumetric Capillary Cytometry" invented by Thomas M. Baer, Louis J. Dietz, Robert S. Dubrow, Paul G. Hayter, Michael Hodges, Bala S. Manian and Robert J. Shartle, owned by the same assignee as this application and incorporated herein by reference. The method and apparatus for gathering and analyzing data to interpret the scans of capillaries as performed by that system is described in co-pending U.S. patent application Ser. No. 08/236,645 entitled "Method and Apparatus for Cell Counting and Cell Classification" invented by Ning L. Sitzo and Louis J. Dietz, also owned by the same assignee as this application and also incorporated herein by reference.

A significant problem confronting the designers and manufacturers of such optical scanners is the inability for different optical scanners to consistently report the same value of fluorescent intensity for the same sample. The fluorescent intensity detected may be useful in determining whether the amount of dye mixed with a sample is appropriate, or in monitoring the continued proper function of the instrument.

Additionally, the absolute intensity value for various areas of high fluorescence, such as cells with dye molecules attached, may provide useful information for diagnostic purposes. Any comparison of fluorescent intensity between tests (or perhaps between optical scanners) requires some standard of absolute fluorescent intensity. However, characteristics of optical components of different optical scanners can vary and, therefore, the different instruments may report different results when scanning the same sample. Without some ultimate reference standard (hereafter "gold standard") against which the different optical scanners may be calibrated, no useful standard of fluorescent units exists for such comparisons.

In addition, the components of the individual optical scanner can change or drift over time and temperature. Furthermore, if one or more of the components of an Optical scanner require repair or replacement, any new or repaired component might vary from the original components, so that the optical scanner no longer reports the same value for the same input.

Some optical scanners currently in use are capable of simultaneously detecting fluorescence in different detectors (channels) where some of the fluorescence from the same dye may be detected in more than one channel at the same time. Such multi-channel optical scanners require an additional calibration. They must be calibrated not only to report standard fluorescent units in each channel, but also to establish the sensitivity of each channel relative to the others.

Each type of fluorescent dye to be detected has a characteristic fluorescent spectrum. The ratio of the fluorescence detected in each channel may therefore be used to identify a particular dye. However, if the detectors change in sensitivity relative to each other, that ratio will appear to change. Improper identification of a dye or the inability to identify the dye can thereby result.

An optical scanner with a plurality of channels as described above is sometimes used to simultaneously detect the fluorescence from two or more types of dye which have different but overlapping emission spectra. In such a case, at least one channel will detect emission from more than one dye. It is possible by analyzing the ratio of the fluorescence detected in each channel to determine which of the dyes was responsible for the emission or if a combination of dyes was responsible for the emission. If the sensitivity of the detectors relative to each other changes, however, this is no longer possible.

To address the problems of a lack of a consistent unit for measuring fluorescent intensity and for adjusting for drift in the sensitivity of multi-channel optical scanners, calibration of the optical scanner is necessary. By calibration, it is meant correlating a device against a reference (standard). Fluorescence spectrometers have historically employed the dye sought to be detected in a sample as a calibration standard for the optical scanner, with the dye being either attached to cells in a blood sample or perhaps to polystyrene beads. However, such dyes have significant shortcomings as calibration standards. For example, the dyes are often unstable and have a limited useful life. In addition, the user is at the mercy of the manufacturer of the dye to assure that the standard is accurate. If it is not prepared precisely the same each time, it will tend to vary in fluorescent response from one dye lot to the next. The dye may also be affected by concentration, the shape, material and other details of the container used to hold the dye, as well as the pH and temperature of the dye, so that even if reliably manufactured, the fluorescent characteristics of the dye may not be uniform and may vary in an unpredictable manner from one use to another. Thus, it is extremely difficult to create a reliable, repetitive standard for calibrating absolute fluorescent units using such dyes. In fact, although it was possible, albeit cumbersome, expensive and generally difficult, to calibrate an optical scanner using dye to determine a ratio of fluorescence detected by the different channels for that dye, it was generally not possible to use these dyes to establish uniform units of absolute intensity, i.e., standard fluorescent units.

Use of such dyes as a standard, even if accurate, often requires extensive, complex and precise preparation and handling which requires significant training, is time consuming, and greatly increases the expense and likelihood of in such a procedure. For these reasons, a relatively stable standard that is easy to handle and predictable in fluorescent response would be a significant advance.

Hence, those concerned with the development and use of fluorescence spectrometers have long recognized the need for improved methods and devices for establishing a uniform fluorescent unit that may be used to meaningfully compare data from different tests and from different fluorescence spectrometers, which may be used to determine a relative sensitivity between channels of a multi-channel detector, and for a stable, permanent calibration standard that obviate the need for a high level of skill, training and expertise, and significant operator input, when performing a calibration on a fluorescence spectrometer. The present invention fulfills all of these needs.

SUMMARY OF THE INVENTION

Briefly, and in general terms, the present invention provides an improved method and apparatus for calibrating a fluorescence spectrometer with reference to a homogeneous solid state standard, that is, a solid state standard with fluorescent particles evenly dispersed at the molecular level. Basically, this may be accomplished in accordance with the invention by exciting the standard to fluoresce, collecting the fluorescence as a beam and directing the beam to a detector that is then adjusted to indicate the fluorescent response of the crystal. The adjustment may be a physical adjustment of the detector or may be a mathematical adjustment to be applied to data reported by the detector.

Temperature variations of a standard at the time of excitation affect the intensity of the fluorescent emission. In accordance with the invention, a temperature sensor is placed in the vicinity of the standard and the temperature is recorded at the time of excitation. Any variation in fluorescent emission due to a difference in temperature can be determined in advance and made available from a look-up table.

One method of calibrating an optical scanner against a gold standard employs an intermediate standard, called here a calibration standard. By way of example, and not necessarily by way of limitation, the calibration standard in accordance with the invention may be rated against the gold standard. In this regard, both standards are excited to emit fluorescence by the same amount of excitation energy as each other, and the intensity of the fluorescence is measured by the same detector. A correction factor is then determined so that the same intensity value of the emission of the calibration standard will be expressed as the same value as that of the gold standard. Thereafter, in any optical scanner calibrated by the calibration standard, the intensity of fluorescence detected by that optical scanner may be adjusted by the correction factor so that the optical scanner will report fluorescent units that may be meaningfully compared to all other optical scanners calibrated by a calibration standard which was calibrated against the same gold standard.

In accordance with the invention, optical scanners with more than one channel may have their different channels calibrated simultaneously with reference to a single standard. This is possible if the fluorescent spectrum of the standard covers a range of wavelengths that is split by a beam splitter into several resultant beams, each resultant beam being directed to a different detector. The intensity of the fluorescence reported by each channel can then be calibrated as described above.

In accordance with the invention, an optical scanner having more than one channel can be calibrated by a single calibration standard to adjust the ratio of the light detected in each channel to compensate for any drift in relative sensitivity between the channels. As a more particular feature of the present invention, a calibration standard is provided which emits fluorescence over a spectral range which includes the wavelengths appropriate for detecting certain useful fluorescent dyes so that the same optical components useful for detecting those dyes may be used to accomplish the calibration of the invention.

Where a crystal is used as a standard, the invention further provides for orientation of the crystal's internal crystalline structure in relation to the excitation source to control the fluorescent intensity and polarization of the standard's emission beam. This may be done, by example, shaping the crystal as a rectangular parallelepiped. The crystal is then fitted snugly into a fixed rectangular depression. When the rectangular depression is located in the. orientation to the excitation beam as in previous scans, the crystal's internal crystalline structure is also aligned in the same orientation.

In a particular application of the invention, ruby has been found to be a particularly useful crystal in that ruby's emission spectrum overlaps with the emission spectra of several dyes useful in conjunction with biological samples and ruby's excitation spectrum is such that ruby may be excited by light of a wide range of wavelengths including most laser light in the visible range. This range of excitation energy includes the excitation energy appropriate for exciting the dyes mentioned above. Thus, an optical scanner for exciting and detecting fluorescence from such dyes may conveniently be calibrated by use of a ruby.

Synthetic ruby is particular is advantageous for use in some optical scanners. Ruby fluoresces at an intensity level that is dependent on the concentration of chromium ions in the crystal, and synthetic ruby's chromium ion concentration may be controlled during manufacture to obtain a ruby having an appropriate concentration for the intended use.

Ruby is very durable and may be conveniently handled and shipped. Ruby is also very stable and will not deteriorate over time. It is not subject to the variables of pH, chemical interactions with surrounding molecules in solution, concentration variance, and the like that have been a problematic source of variability in other fluorescent material previously used as a standard. It may be reliably reproduced and even synthetically prepared to have appropriate fluorescent intensity. The ruby may be permanently built into an optical scanner for repeated use, routine and automatic use.

The new and improved method and device of the present invention provides a convenient, reliable and inexpensive way to calibrate fluorescence spectrometers to provide for standard units of fluorescent intensity to calibrate the balance of sensitivity to fluorescence between channels of a multi-channel fluorescence spectrometer, and to do so by means of a stable, sold and permanent calibration standard that may be constructed as part of the fluorescence spectrometer to provide for simple, automatic, frequent and inexpensive calibration of the instrument.

These and other objects and advantages of the invention will become apparent from the following detailed description, taken in conjunction with the accompanying drawings, which illustrate, by way of example, the features of the invention.

DESCRIPTION OF THE DRAWINGS

FIG. 5 is a top plan view of a platter for use in an optical scanner showing a built-in calibration ruby in accordance with the invention;

FIG. 6 is an enlarged top plan view of the dash-circled area in FIG. 5 showing the calibration ruby;

FIG. 9 is a temperature look-up table for use with the invention;

FIG. 11 is a flow chart of the procedure for automatically setting an optical scanner's sensitivity to fluorescence whenever power to the optical scanner is turned on;

DETAILED DESCRIPTION OF THE PREFERRED EMBODIMENT

Figure 1:
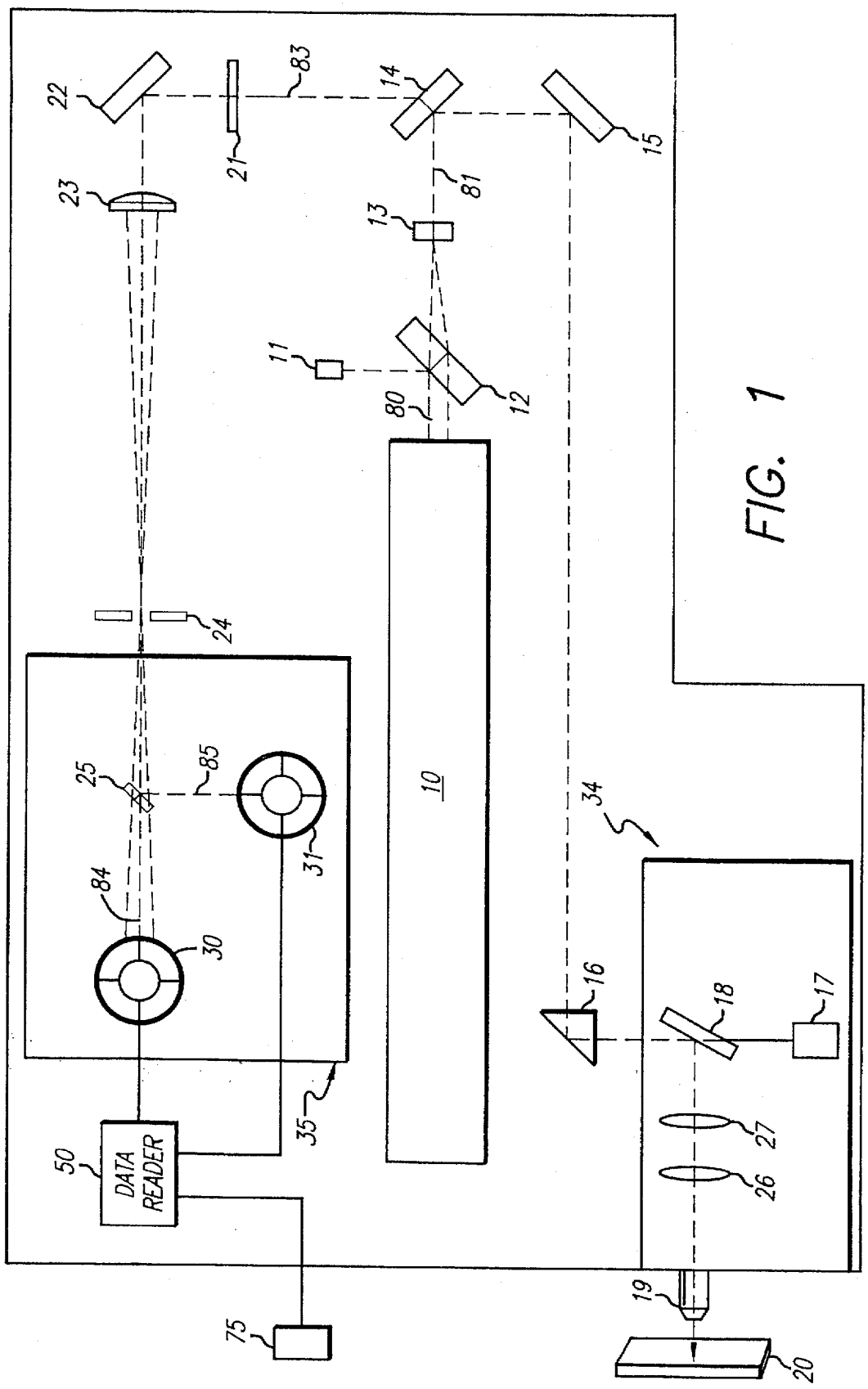
FIG. 1 is a system diagram of an optical scanner for use with the invention.

The calibration method and apparatus of the present embodiment may be used on an optical scanner of the type disclosed in U.S. patent application Ser. No. 08/236,342 entitled "Apparatus and Method for Volumetric Capillary Cytometry" invented by Thomas M. Baer, Louis J. Dietz, Robert S. Dubrow, Paul G. Hayter, Michael Hodges, Bala S. Manian and Robert J. Shartle, owned by the same assignee as this application. It is designed to be used in conjunction with the method and apparatus for interpreting data as disclosed in U.S. patent application Ser. No. 08/236,645 entitled "Method and Apparatus for Cell Counting and Cell Classification" invented by Ning L. Sitzo and Louis J. Dietz, also owned by the same assignee as this application.

The optical scanner for use with the invention, described with reference to FIG. 1, includes a laser 10, such as a helium neon laser (hereafter, HeNe laser), which generates a laser beam 80 that impinges on a glass plate 12. The glass plate reflects a significant portion of the laser beam 80 to a power monitor 11 which measures the power output of the laser. The portion of the excitation beam 81 that is passed through rather than reflected by the glass plate 12 is directed through a laser line filter 13 and then to a spectral dispersion device 14, which may be, for example, a dichroic mirror, a prism, or a grating. The spectral dispersion device 14 reflects the excitation beam 81 which, in the case of a HeNe laser, has a wavelength of approximately 633 nanometers.

The excitation beam 81 is then directed to a mirror 15 and reflected by that mirror to a right angle prism 16. The beam travels through the right angle prism to a scan assembly 34.

The scan assembly 34 comprises a galvanometer 17, a galvo mirror 18, lenses 26 and 27, and an objective lens 19. The galvanometer 17 is in communication with the galvo mirror 18 to oscillate that mirror while the excitation beam 81 is directed onto the galvo mirror. The excitation beam 81 is thereby scanned across objective lens 19. The excitation beam 81 is directed through the objective 19 lens and thereby scanned across a capillary 20. The capillary 20 contains within it, for example, a biological sample 53 stained with fluorescent dye in it.

Figure 2:
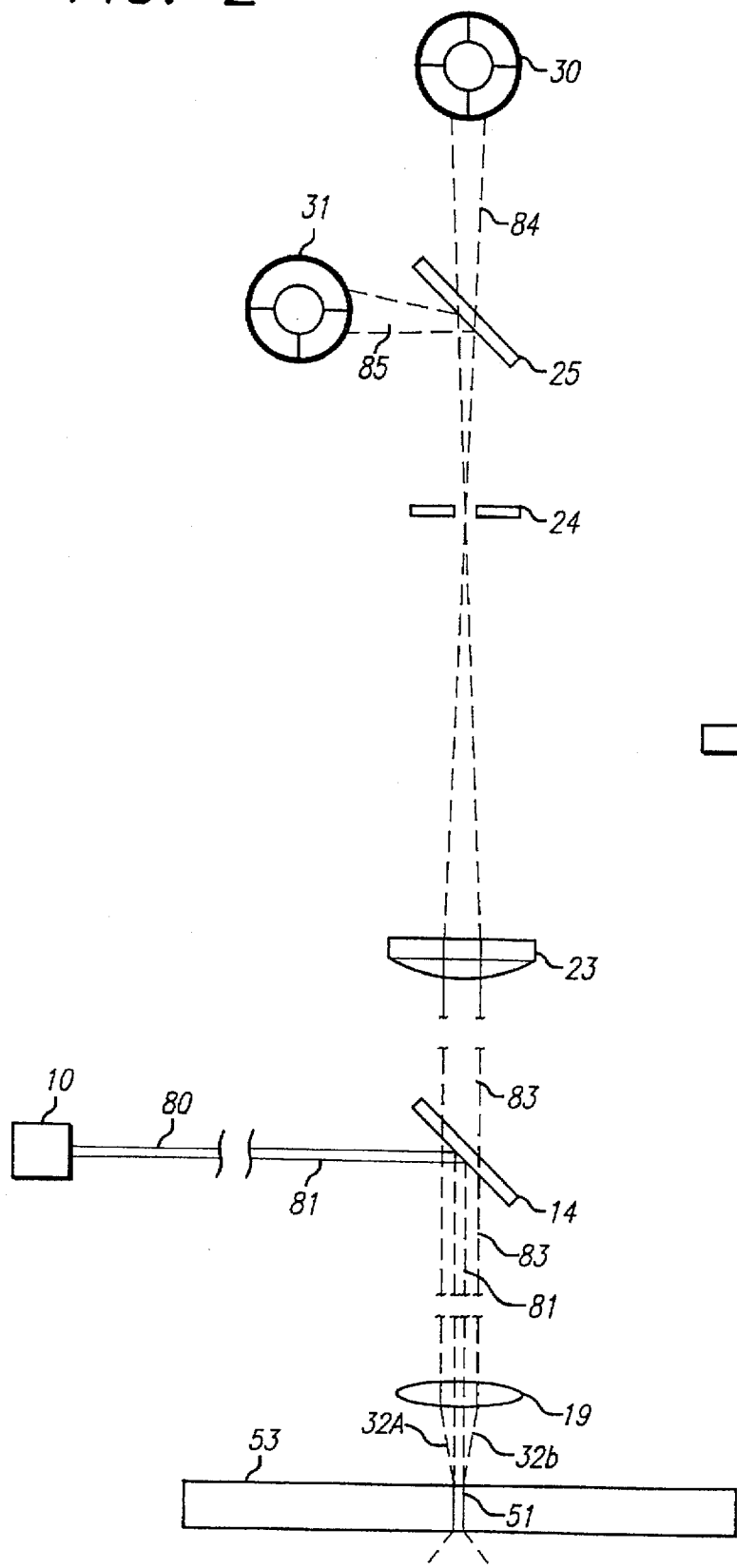
FIG. 2 is a schematic diagram illustrating capillary being scanned by the optical scanner of FIG. 1.

As best observed in FIG. 2, during a sample scan, the excitation beam 81 impinges upon the outer wall of the capillary 20, traverses the wall, and illuminates a columnar region 51 of the sample 53 causing fluorescent emissions from the sample. The fluorescent emissions from the sample are represented in FIG. 2 by the rays 32A and 32B. Some of the fluorescent emissions thus generated fall on the objective lens 19 and are collected and directed back from the sample as a retrobeam 83.

Fluorescence emitted by the sample as a result of excitation and collected by the objective lens 19 is directed back through scan assembly 34. Referring now more particularly to FIG. 1, the retrobeam 83 travels from the scan assembly 34 through the right angle prism 16 to the mirror 15 and the spectral dispersion device 14. The retrobeam has a spectral range which encompasses different wavelength than the excitation beam, and may therefore be directed differently than the excitation beam by the same optical components that direct the excitation beam to the scan assembly 34. For example, due to its wavelength, the retrobeam 83 is transmitted through the spectral dispersion device 14 rather than reflected by that device, and then through a bandpass filter 21 to a mirror 22 where it is directed through a collimating lens 23.

Any light having the wavelength of the excitation beam 81, for example light from the excitation beam reflected by the capillary 20 surface back along the path of the retrobeam 83, will be reflected by the dichroic mirror 14 away from the path of the retrobeam and back toward the laser 10. The retrobeam 83 is thereby purged of reflected excitation light. The retrobeam 83 is focused by the collimating lens 23 through a pinhole aperture of a spatial filter 24 which acts to eliminate from that retrobeam any light other than fluorescent emissions from a defined region 51 within the scanned object.

After passing through the spatial filter 24, the that retrobeam 83 is directed to a detection means 35. The detection means 35 comprises a detection channel such as PMT 30 which receives the fluorescent signal of the retrobeam 83, amplifies the signal received, and reports the amplified results to data reader 50 which converts it from analog to digital form and records it in units of fluorescence intensity. For purposes of this description, those units are denominated as analog to digital counts, or "A/D cts".

The detection means 35 contains two detection channels, each channel having its own PMT 30, 31. A spectral dispersion device 25 may be positioned between the spatial filter 24 and PMTs 30 and 31 to split the retrobeam 83 based on the wavelength of the light, and to direct one beam 84, to the first PMT 30, and the other beam 85, to the other PMT 31. In this manner, the single optical scanner has two channels, each of which receives a distinct portion of retrobeam 83.

With reference to FIG. 5, the capillaries 20 are each carried by a cartridge 49, with each cartridge carrying two capillaries. The cartridge 46 is laid on a rotating platter 48 rotates beneath the objective 19. A motor (not shown) rotates the platter 48 to position each capillary 20 beneath the objective 19 and pauses while the capillary is beneath the objective until a scan on that capillary is complete. The motor then rotates the platter 48 again until the next capillary 20 is beneath the objective 19, and a scan of that capillary may then be performed.

Referring now to FIGS. 5 and 6, the platter 48 is designed to hold ten cartridges 49 and contains ten radial support arms 46. A calibration crystal such as ruby 45 is installed in one of those support arms 46. In order to scan the calibration ruby 45, the platter 48 is rotated and stopped in a position where the calibration ruby is beneath the objective lens 19. The ruby 45 is then excited with an excitation beam 81 from laser 10 and the fluorescence emitted as a result is collected as a retrobeam 83 and divided to and detected by the channels 30, 31 of the optical scanner. In practice, an average maximum value for fluorescent intensity detected as a result of this ruby scan may be obtained by sequentially scanning a number of points on the ruby and averaging the maximum value of fluorescent intensity from each scan in order to obtain an average value which is then used for purposes of the calibration. This enhances the dependability of the value used.

Unlike performing a scan on a sample 53, when performing a scan of a ruby 45, the galvo mirror 18 is stationary. A ruby has a relatively long period of fluorescence after excitation. The optical scanner senses fluorescence from the ruby back through the same objective 19 used to focus the excitation beam 81 onto the ruby 45. Thus, the fluorescence detected will be from the same spot and at the same time as the excitation beam 81. If the galvo 18 oscillated as it does when the excitation beam 81 is scanned across a capillary 20, the measured signal from the ruby 45 would be greatly attenuated since the point of detection would have moved on before the ruby 45 reaches a steady state of fluorescent emission.

Optical scanners with a plurality of detection channels are useful in identifying fluorescence from different dyes. For example, in the simplest case, a sample might contain two dyes which fluoresce with spectra having a range of wavelengths such that a retrobeam 83 comprising light from the fluorescence of those two dyes is split by a spectral dispersion device 25 into separate and distinct beams 84, 85, each representing florescence from one and only one dye and each directed to different PMT 30, 31. In such a case, all the fluorescence detected by one particular channel represents fluorescence from one particular dye, and all the fluorescence detected by the other channel would represent the other dye. Using a single excitation beam 81 and performing a single scan, these two different dyes could easily be detected and distinguished by splitting the retrobeam 83 and directing the resultant beams 84, 85 into separate channels.

In a more typical case, however, the fluorescence of the retrobeam 83 is comprised of fluorescence emitted by two different dyes with overlapping emission spectra such that a portion of the fluorescence of at least one of the dyes is directed to both of the two channels. In such a situation it is still possible to determine if one dye or the other or a combination of both is responsible for the fluorescence detected by the two channels of the optical scanner. This requires a determination of the ratio of the total fluorescent energy directed to the two different channels. This may be done by determining a ratio of what portion of the fluorescence of each dye is directed to each channel, and analyzing the relative amount of fluorescent emission detected by each channel.

Figure 8:
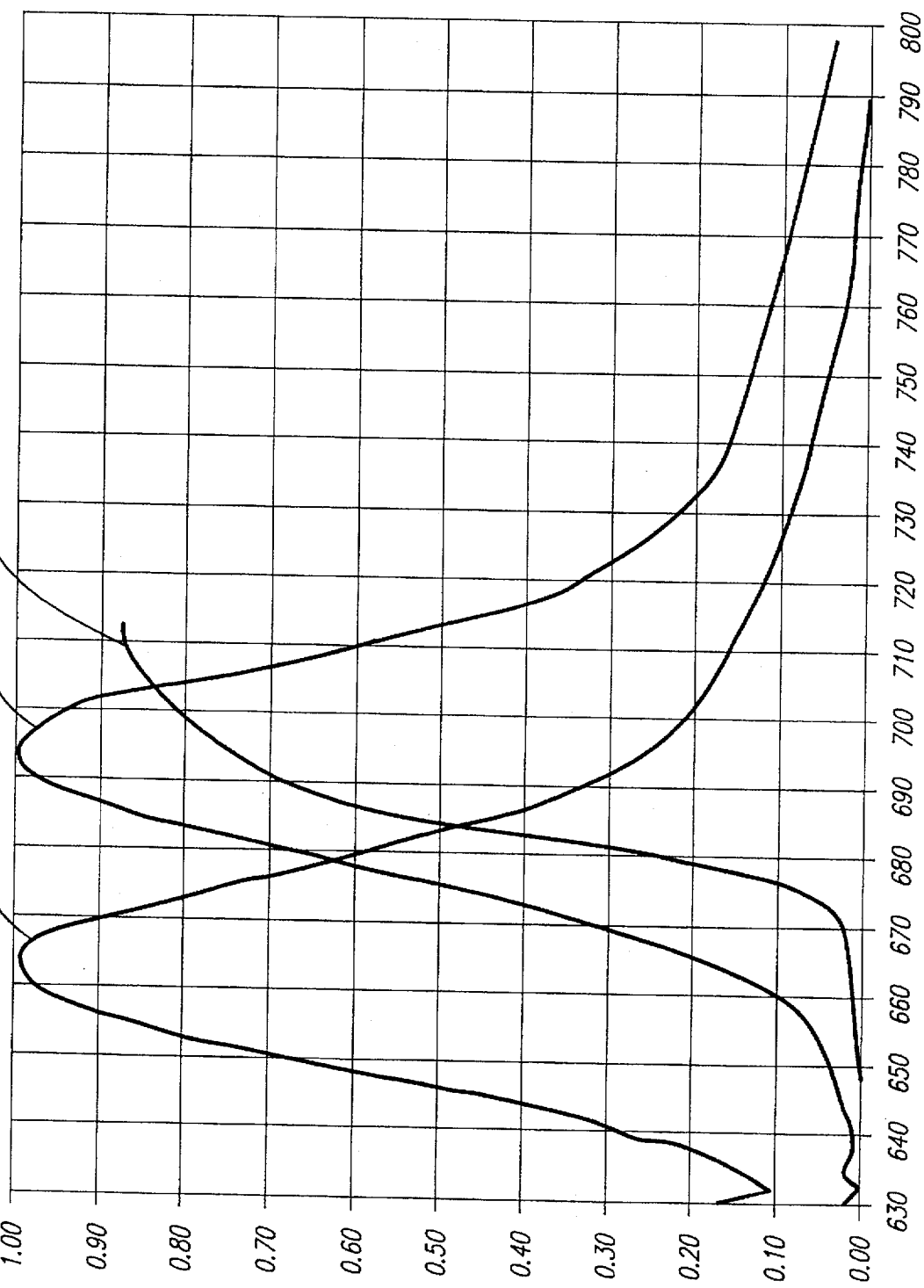
FIG. 8 is a graph illustrating the emission spectra of two different dyes and the transmission spectrum of a dichroic mirror which divides the emission spectra of the dye.

An example of such a situation would be a sample containing cells labeled with both Cy5™ dye and Cy5.5™ dye. The Cy5™ dye is a reactive cyanin with fluorescence characteristics similar to allophycocyanin having a molecular weight less than one-thousand. It is a succinimidyl ester provided as a dried dye ready for labelling of compounds containing free amino groups and is available from Biological Detection systems, Inc., of Pittsburgh, Pa. It has an absorption maximum at 652 nanometers and an emission maximum of 667 nanometers and an emission spectrum from about 630 nanometers to about 800 nanometers as shown by line 91 in FIG. 8. Cy5.5™ is a similar dye, also available from Biological Detection Systems, Inc., of Pittsburgh, Pa., with an emission maximum at about 695 nanometers and a spectral range of about 650 nanometers through about 780 nanometers as shown by line 93 in FIG. 8. If a retrobeam comprised of fluorescence from these two dyes is directed to a spectral dispersion device which separates the fluorescence into two beams, one having wavelengths greater than, and one less than, approximately 684 nanometers, as shown by line 95, and the resultant beams directed to different channels 30, 31, a portion of the fluorescence of each of the dyes will be directed into each of the channels.

Figure 7A:
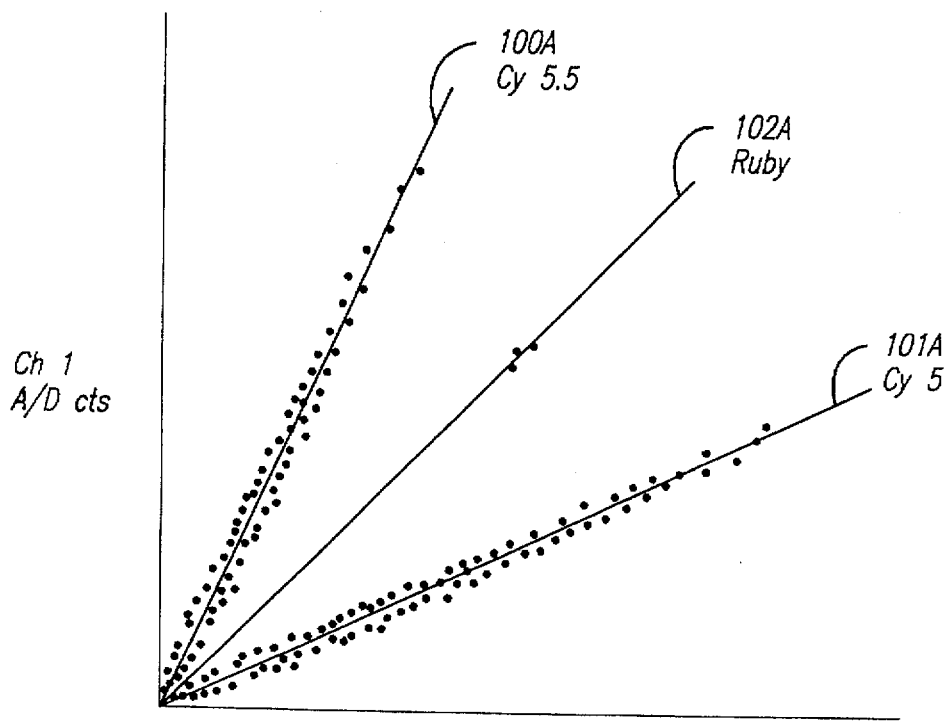
FIG. 7A is a graph illustrating fluorescent units detected by the scanner of FIG. 1 with the fluorescent units detected by channel one graphed against the fluorescent units detected by channel zero.

Each dye may be identified by means of the characteristic ch1/ch0 ratio of its fluorescence. That ratio is of the amount of fluorescence which is directed into each channel as described above. The ratio is characteristic of the dye which is fluorescing and may be graphed as shown in FIG. 7A with the fluorescent units detected by channel one (ch1) being the Y axis and the fluorescent units detected by channel zero (ch0) being the X axis.

The characteristic ratio for each dye results in all fluorescent emissions from that dye being graphed along a line with the slope of that line being the ratio, and the point along the line being the total fluorescent energy detected. For example with reference to FIG. 7A, line 100A shows such a graph of fluorescent units of an emission from Cy5™. The slope of that line represents the ratio of fluorescent energy going into ch1 relative to ch0 (i.e., ch1/ch0). Another such line is shown in FIG. 7A as 100A which represents, for example, the fluorescent emission for Cy5.5™. The ratio for each dye is characteristic of that dye, and a detected emission may be graphed as shown. If the fluorescence emission graphed falls along the characteristic line for a particular dye, it may be properly identified as being emitted by that dye.

Figure 7B:
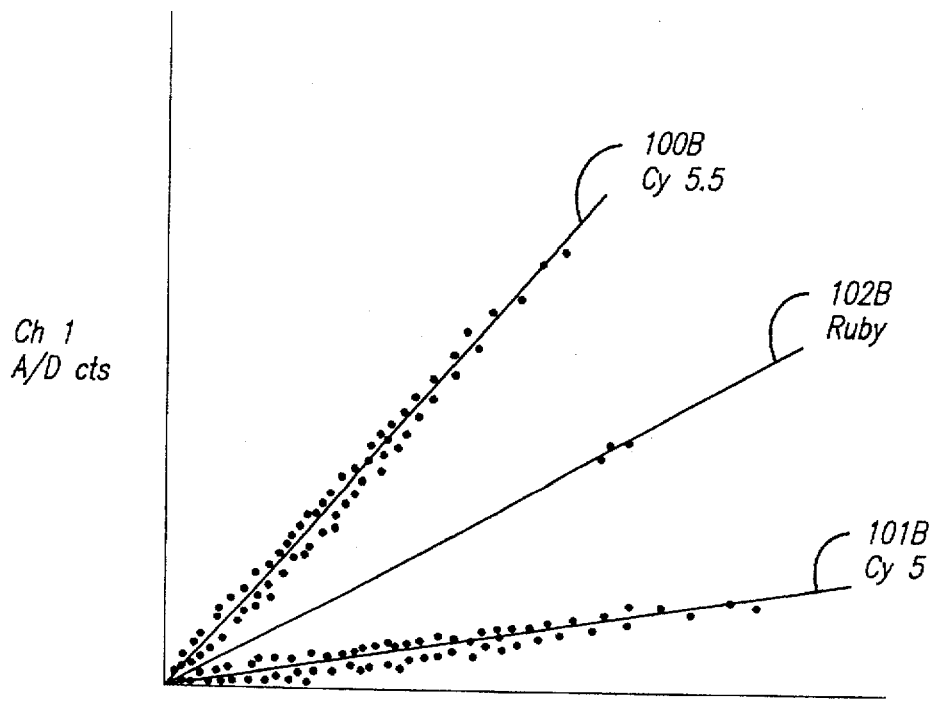
FIG. 7B is a graph illustrating the same data as illustrated in FIG. 7A, but detected by the same two channels of a scanner as in FIG. 7A after a change in relative sensitivity between the channels.

However, if the relative sensitivity of the channels 30, 31 changes over time, as may sometimes occur where PMTs are used as detectors, or other optical elements such as mirrors or lenses are smudged or otherwise change over time, the apparent ratio of the light directed to each channel will change. Such a change is demonstrated with reference to FIG. 7A and 7B. Line 100A in FIG. 7A represents the ratio of ch1/ch0 observed by a particular optical scanner for fluorescent emissions from Cy5™. Line 100B in FIG. 7B illustrates that same ratio observed in the same optical scanner after a change in relative PMT sensitivity. The optical scanner may still direct the same proportion of the fluorescent emission to each channel, but because of the relative change in sensitivity of the channels, the ratio will appear to have changed, and a graph of emissions from Cy5™ 100B will then show a line with a slope different than was previously the case. Other characteristic emission Spectra detected by the same optical scanner and graphed will experience the same apparent shift in the characteristic slope of their lines as shown by lines 101A in FIG. 7A and 101B in FIG. 7B, representing the ch1/ch0 ratio for Cy5™.

Crystals such as ruby, or glass doped with ions such as chromium ions, also have a characteristic fluorescence spectrum and, when detected by a two channel optical scanner, may also be identified by their characteristic ch1/ch0 ratio. This may be graphed as illustrated by line 102A in FIG. 7A. When the sensitivity of the detectors change, the apparent ratio of ch1/ch0 for the ruby emission also changes. That will change by the same degree as all other characteristic emissions detected by the same optical scanner. Therefore, by reference to the apparent change in the slope of the ruby emission line, the slope of the lines for emission of other dyes may be determined so that such emissions may be properly identified. This may be done without the need to run a calibration cartridge containing pure dye, since, if the shift in the slope of the ruby ch1/ch0 line is known, it may be used to determine the shift in the ch1/ch0 lines for all other emissions. Ruby, which is a crystal of sapphire doped with chromium ions, has an emission spectrum that is excited, split, and detected by the same optical components of an optical scanner that are useful to analyze many dyes useful to stain biological specimens such as Cy5™ and Cy5.5™ described above. The emission spectrum of ruby is relatively narrow, between 692 nm and 694 nm, and will pass through the spectral dispersion device 14 in the same manner as a retrobeam 83 generated by the fluorescent emissions of Cy5™ and Cy5.5™. The same spectral dispersion device 25 of the preferred embodiment which splits the retrobeam beam 83 from Cy5™ and Cy5.5™ will also split a retrobeam 83 generated by the ruby. The precise ratio by which the ruby retrobeam 83 is divided is not critical, but for purposes of illustration in FIG. 7A it is shown as about 50/50, with each resultant beam 84, 85 directed to a different channel 30, 31. A graph of the ch1/ch0 fluorescent units for ruby is represented by line 102A in FIG. 7A. When the relative sensitivity of ch1 and ch0 changes, the apparent slope of line 102A will also change as is illustrated by the change from 102A in FIG. 7A to 102B in FIG. 7B. The slope of these lines will change by the same factor as slope of the lines for Cy5™ and Cy5.5™. Thus, by reference to the apparent change in the calibration ruby's ch1/ch0 ratio, the apparent change in the ratio of ch1/ch0 for other dyes as detected by the same optical scanner may be determined and the observed data adjusted appropriately.

The intensity of the fluorescent response of the ruby to excitation is dependant on the concentration of chromium ions in the ruby crystal. If the crystal contains too high a concentration of chromium ions the fluorescent light has too great an intensity and the beams 84 and 85 saturate the detectors 30, 31. The concentration of chromium ions in synthetic ruby can be controlled during the manufacture of the synthetic ruby so a ruby with the appropriate concentration of chromium ions for the fluorescent intensity desired may be obtained. The ruby 40 of this embodiment is manufactured with a relatively low concentration of chromium ions, for example, of 37±12 parts per million.

The built-in calibration ruby 45 is relatively thin, generally between 0.5 mm and 1.0 mm thick. During a scan, the excitation beam 81 is directed to the ruby through the objective lens 19 that focuses to a gaussian waist 51, which is 10 microns in diameter and 100 microns deep. The excitation beam 81 is able to excite a maximum emission from any ruby that is over 100 microns in depth, in other words, whenever the entire gaussian waist is within the ruby 40. During a scan, the objective lens 19 is gradually moved toward the ruby 40, moving the gaussian waist through the ruby in order to determine a maximum emission value. Maximum excitation is achieved whenever the gaussian waist is fully contained within the crystal. As the focal area (i.e., gaussian waist) of the objective is moved beyond the far surface of the ruby, the fluorescence emitted begins to diminish. Thus, the software detecting the emission is able to determine that the detected emission value has increased, stabilized for a time at a maximum value, and then begun to decrease. The software may thus select the highest value achieved as the maximum value with confidence that the value would not have increased had the ruby scan continued.

The alignment of the ruby's crystalline structure with respect to the excitation beam 81 affects both the intensity of the fluorescence and the wavelength at which the spectral dispersion device 25 splits the emitted beam 83. In ruby, for example, the intensity of the emitted light can vary by as much as a factor of three depending on the ruby alignment relative to the excitation beam 81. Although the change in intensity does not affect the spectral range of emission of the ruby and therefore does not significantly affect the ratio of the emitted light that is detected by each of the channels 30, 31, the overall intensity detected will vary. Since data concerning absolute intensity observed is important for monitoring the continued proper function of the equipment and the appropriate level of dye mixed with the sample 53 and may generate useful diagnostic information, absolute intensity should be calibrated from time-to-time. In order to calibrate the optical scanner for sensitivity to fluorescent intensity, alignment of the calibration ruby's crystalline structure must be the same each time relative to the excitation beam.

The alignment of the crystalline structure relative to the excitation beam is also important to generate emissions having the same polarization each time. The wavelength at which a dichroic mirror 25 splits the spectral emission from the ruby varies depending on the polarization of the light striking the mirror. Thus, in order to maintain consistency in the ch1/ch0 ratio from scan to scan, all other factors being equal, the polarization of the emitted fluorescence must be the same each time. The polarization of the emitted light varies depending on the alignment of the crystalline structure. Therefore, for this reason as well as the intensity of the fluorescent emission, the alignment of the crystalline structure must be consistent from scan to scan.

Figure 4:
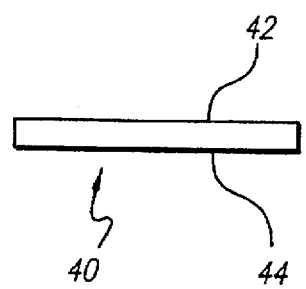
FIG. 4 is a side elevation view of a ruby in accordance with the present invention.

Both of these concerns of surrounding crystalline alignment, intensity and polarization, are solved by the shape of the ruby. Referring now to FIG. 4, the ruby 40 is a rectangular parallelepiped. The crystalline structure of the ruby 40 is specified in relation to the parallel sides of the rectangle. For example, the ruby 40 may be obtained with the crystalline optical axis 60°–65° from the polished surface 42 normal. Referring to FIG.5, the ruby 40 is rectangularly shaped and sized to fit snugly in a rectangular depression in a support arm 46 of the platter 48. Light emitted by the ruby 40 rotates in polarization once for each 180° rotation of the crystal, so when the rectangular ruby 40 is inserted in a rectangular depression in the support arm 44, the ruby can only be orientated in two possible orientations, and either will result in the same polarization of the light being emitted by the ruby. The relatively thin ruby may also be rotated 180° with either of the large faces positioned as the top face. This also results in an orientation of the internal crystalline structure that produces light with the proper polarization.

Figure 3:
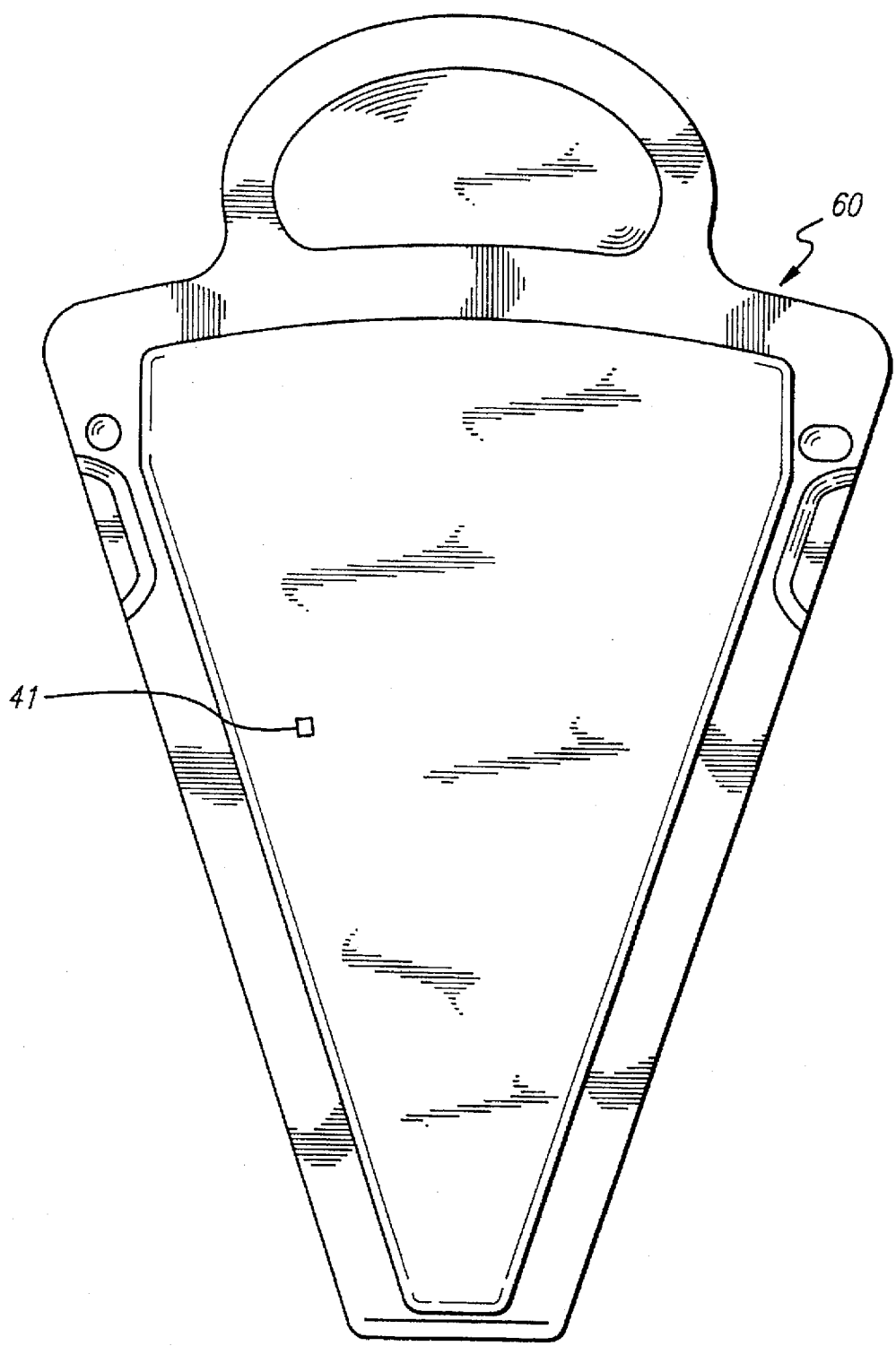
FIG. 3 is a top plan view of a cartridge containing a gold standard ruby in accordance with the invention.

A similar method of orientating the ruby in a predictable manner may be employed for the gold standard ruby 41. Instead of being inserted in a rectangular depression located in a support arm 46 in the platter 48 as is the calibration ruby 45, the gold standard ruby 41 may be similarly shaped and located snugly in a rectangular depression in a cartridge 60 as is illustrated in FIG. 3, with the ruby 41 located on the cartridge where a portion of capillary 20 is located on sample cartridge 49. The cartridge 60 may be placed on the platter 48 in the manner of cartridges 49 for scanning.

Referring now to FIG. 1 and FIG. 2, when a scan is performed on a ruby, either on the gold standard ruby 41 (FIG. 3) or the calibration ruby 45 (FIG. 6), the ruby is placed below the objective lens 19 and an excitation beam 81 is directed onto the ruby, the galvo mirror 18 being stationary. The excitation beam 81 causes the ruby to fluoresce with a spectrum over the wavelengths of 692 nanometers through 694 nanometers. The fluorescence is collected by the objective lens 19 and directed back toward the detection means 35 as a retrobeam 83. When it impinges on the dichroic mirror 14, the beam is not reflected but rather is transmitted through the dichroic mirror and from there through the bandpass filter 21 to the mirror 22. It is reflected from mirror 22 through collimating lens 23 and thereafter through the spatial filter 24 and into the detection means 35.

The detection means 35 constitutes at least one detection channel such as PMT 30 which reads the fluorescent signal of the retrobeam 83 and is in communication with data reader 50 which converts the signal reported from the PMT from analog to digital form. In the detector illustrated in FIG. 1, retrobeam 83 is directed a spectral dispersion device 25 which splits the retrobeam into resulting beams 84, 85, each of which are then directed to separate detection channels 30, 31, respectively. The signal generated by each PMT is read by the data reader in units of fluorescence intensity, which may be referred to as A/D cts, which refers to the data in analog form from the detector that are converted by the data reader to digital data counts.

The optical scanner may be directly calibrated against a gold standard ruby 41 to report standard fluorescent units. By doing so, standard fluorescent units for measuring absolute fluorescent intensity may be established among all optical scanners calibrated against the gold standard ruby 41.

In practice, the optical scanners are indirectly calibrated against the gold standard ruby 41; a calibration ruby 45 built into the optical scanner is rated against the gold standard ruby. When the optical scanner is subsequently calibrated against the built-in calibration ruby 45, the optical scanner may be adjusted to report standard fluorescent units, as established by the gold standard ruby 41.

This calibration to report standard fluorescent units by a particular optical scanner is performed as follows. A calibration ruby 45 is built into the support arm 46 of the platter 48. The platter is rotated until the calibration ruby is located directly under the objective 19 of the optical scanner. The platter then stops rotating and the calibration ruby is stationary under the objective. A beam from laser 10 is directed onto the ruby, which emits fluorescence as a result. The fluorescence emitted from the calibration ruby 45 is collected into a retrobeam 83 and is directed to the detector, or in a two-channel optical scanner, each detector 30, 31. The maximum fluorescent value, also known as peak Value, of the calibration ruby 45 fluorescence is determined.

Each detector 30, 31 is a photomultiplier tube (PMT) whose sensitivity may be adjusted by adjusting the voltage applied to its bias. When the fluorescence emitted by the calibration ruby is detected, the bias voltage is adjusted until its sensitivity to the maximum detected fluorescence is within a predetermined range, for example about 1000 A/D counts. In a two-channel detector, the same procedure may be used to initially set the bias as to each channel.

Thereafter, a gold standard ruby 41, generally located on a cartridge 60, as is illustrated in FIG. 3, is placed on the platter 48. The platter 48 is rotated until the gold standard ruby 41 is located directly under the objective 19. The platter 48 then stops rotating and the gold standard ruby 41 is stationary under the objective 19. An excitation beam 81 from laser 10 is directed onto the gold standard ruby 41 which emits fluorescence as a result. The fluorescence emitted by the gold standard ruby 41 is collected into a retrobeam 83 and directed to the detector or detectors 35, as was the retrobeam of the calibration ruby 45. The maximum intensity of the gold standard ruby 41 fluorescence (peak value) is then determined and the calibration ruby 45 is then rated against the gold standard ruby 41 by determining a factor by Which the fluorescent units of the calibration ruby 41 peak value may be converted into fluorescent units of the gold standard ruby 41 peak value. This adjustment may be made to the sensitivity of the detectors, as by adjusting the bias voltage on a PMT, or may be a mathematical correction applied to data derived from the optical scanner.

The intensity of fluorescent emission of a ruby is affected by temperature. For example, over a range of 15° C. to 35° C., the signal amplitude may vary as much as 30% in each channel. It is therefore necessary to determine the temperature of the calibration ruby 45 at the time of its rating against the gold standard ruby 41 and again later whenever the optical scanner is calibrated against the calibration ruby 45, in order to compensate for any difference. The adjustment appropriate for a particular temperature variation is available by reference to a look-up table. For the ruby described in this embodiment, the look-up table was determined experimentally, normalized against a temperature of 25° C., and a factor for normalizing the intensity is listed, ranging from a factor of 0.71 for 5° C. and 1.30 for 45° C. The look-up table is shown in FIG. 9.

In practice, it has been found to be adequate to measure the temperature of the immediate environment of the ruby 45, such as the interior of the optical scanner generally, rather than directly measure the temperature of the ruby itself, provided sufficient time and exposure are provided to allow the ruby to achieve approximately the same temperature as its environment. Therefore, it has been found to be adequate to place a temperature sensor 75 within the optical scanner and not directly measure the temperature of the calibration ruby 45. The calibration ruby 45 is mounted on the platter 48 that rotates as part of the scan procedure, and the gold standard ruby 41 is on a cartridge 60 which is placed on platter 48 and also rotates in use. A temperature sensor 75 that does not need to directly measure the temperature of a ruby that must be free to rotate has been found to be more convenient and less expensive to manufacture and operate than a temperature sensor which directly measures the temperature of such a ruby.

If the scanner has two channels, both may be simultaneously calibrated by means of a single calibration ruby 45. The stimulation of the calibration ruby 45 and the generation of a retrobeam 83 thereby are as described above. When the retrobeam 83 is directed to spectral dispersion device 25, such as a dichroic mirror, the beam is separated into resultant beams 84 and 85 which are directed to two detectors 30 and 31, such as PMTs. Each of these resultant beams may then be used to set the sensitivity of PMTs 30, 31 by adjusting their bias voltage. Thereafter, a gold standard ruby 41 is scanned, its retrobeam 83 is similarly split and the resultant beams 84, 85 directed to the PMTs 30, 31 and the intensity of each recorded for each channel. A compensation factor for each channel 30, 31 is then determined by which the emission of the calibration ruby 45 is calibrated against the gold standard ruby 41 to obtain a value by which the calibration ruby may be rated so that its output will report standard units of absolute fluorescent intensity. Thereafter, when the calibration ruby 45 is scanned, both channels 30, 31 may be calibrated simultaneously to report standard fluorescent units as determined by reference to the gold standard ruby 41.

Referencing FIGS. 7A and 7B, where two dyes with overlapping spectra such as Cy5™ and Cy5.5™ are detected in a two channel optical scanner such as that illustrated in FIG. 1, changes over time in the sensitivity of one or both of the channels will result in changes in the apparent ch1/ch0 ratio of fluorescent signal for each. The ruby emission's ch1/ch0 ratio will experience a like apparent change, but the three ratios will remain constant relative to each other. Since identification of the relevant dye (and thus the cell on which it is concentrated) depends on an accurate determination of the characteristic ch1/ch0 ratio, it is necessary to accurately determine that ratio at the time of any test to assure proper identification of the dye and thus the cell. This may be done by reference to fluorescent emissions from the calibration ruby 45. Put another way, if the ch1/ch0 ratio for any dye has an apparent change due to changes in channel sensitivity, the ruby emission will have an apparent change in its ch1/ch0 ratio by the same factor. Therefore, the correct ch1/ch0 ratio for any dye may be determined after an apparent change if the ch1/ch0 ratio for that dye was determined relative to a ch1/ch0 ratio of the calibration ruby 45. The ch1/ch0 ratio of the ruby after the apparent change can then be determined, and the change apparently experienced between the original ch1/ch0 ratio for the ruby and for the dye will be the same.

In practice, several different calibrations of the optical scanner may be performed, all with reference to the synthetic ruby standard. Initially, the optical scanner is calibrated against a gold standard ruby 41 to set sensitivity to fluorescent intensity that provides a uniform standard of fluorescent units for all optical scanners calibrated directly or indirectly against the gold standard ruby 41. In addition, a calibration ruby 45 may be supplied with each optical scanner and calibrated against the gold standard ruby 41. That calibration ruby 41 can then be built into the optical scanner so that the optical scanner may routinely and automatically (for example, whenever the optical scanner is turned on) be calibrated with reference to the calibration ruby to accurately report fluorescent units that represent standard fluorescent units. If a two channel detector is provided and the spectral emission of the ruby is divided into two beams 84, 85, each directed to two different channels 30, 31, both channels can be calibrated simultaneously by reference to a single ruby crystal. Even if no absolute calibration of each of the two channels is made, a ch1/ch0 ratio for the ruby can be determined and subsequent adjustments made, physically or mathematically, to adjust for any changes in the relative sensitivity of the two channels.

Figure 10:
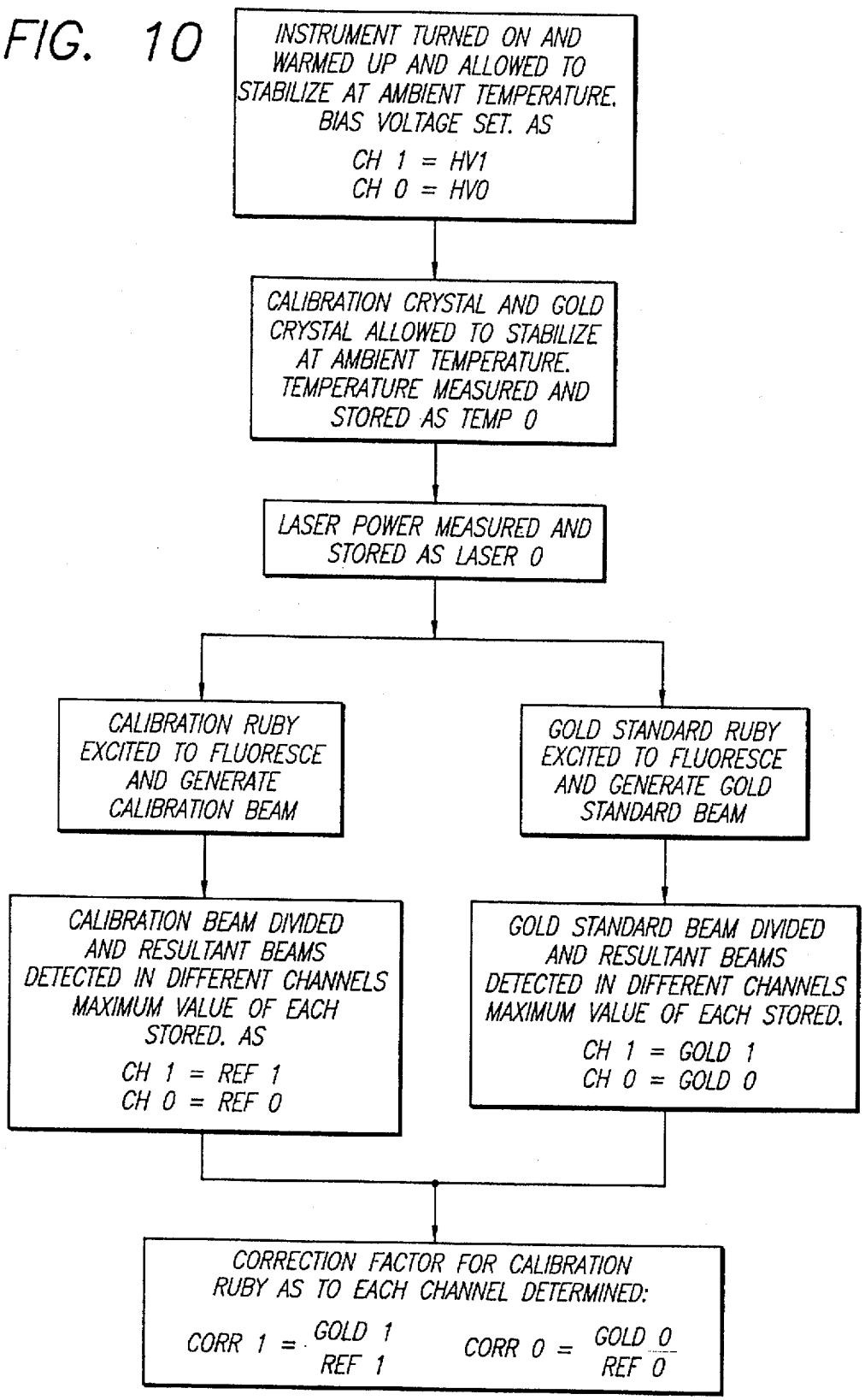
FIG. 10 is a block diagram showing the steps involved in determining the of fluorescent intensity of a calibration ruby by reference to a gold standard ruby.

Referring now to FIG. 10, a method for indirectly calibrating an optical scanner against a gold standard ruby 41 by comparing the fluorescence emitted by a calibration ruby 45 with that emitted by the gold standard ruby 41, determining a correction factor applicable to the calibration ruby 45, and subsequently calibrating the optical scanner against the calibration ruby 45 and adjusting the optical scanner by reference to the correction factor to obtain a setting of standard fluorescent units is shown. This method is described here with reference to a two-channel detector and with reference to the measurement of the fluorescent intensity from the calibration ruby 45 prior to the measurement of the fluorescent emission from the gold standard ruby 41. It will be readily appreciated by those of skill in the art, however, that the calibration for use in a single channel detector is similar. It will also be readily perceived by one of ordinary skill in the art that the order of detecting fluorescence may be either with fluorescence from the calibration ruby 45 detected first, or from the gold standard ruby 41 detected first.

To begin the calibration, the optical scanner is turned on and its components, specifically the laser 10, PMTs 30, 31, the temperature sensor 75, and the calibration ruby 45 are allowed to warm up. This provides for a relatively stable temperature during the calibration. The detectors of each channel 30, 31 are each set to an initial sensitivity. For future reference, this value may be stored for use during the automatic adjustment when the optical scanner is first turned on. In the case of PMTs, the sensitivity is adjusted by means of the bias voltage, and it is the value of this voltage that may be recorded for later use. For the discussion here, the bias voltages of ch1 and ch0 will be referred to as hv1 and hv0, respectively. The laser is turned on and its power is measured with built-in photodiode 11 and the laser power is then stored. For the discussion here, this laser power value is referred to as laser0.

The laser 10 then generates an excitation beam 81 which is then directed to the calibration ruby 45 and the fluorescence thus generated is collected as retrobeam 83 and directed to the detectors 30, 31. The maximum signal for each channel is then recorded. For the discussion here, this maximum sensed value is referred to for channel 1 as ref1 and for channel 0 as ref0.

The temperature is read from the temperature sensor, and recorded for later use. For the discussion here, this will be referred to as temp0.

The gold standard ruby 41, which may be mounted in a plastic cartridge 60, is located under the objective 19, excited to fluoresce by excitation beam 81, the emitted fluorescence is divided by the same optical components as was the case for the calibration ruby 45 in the previous paragraph, and the maximum signal for each channel is then recorded. These maximum values for the signal sensed in ch1 and ch0 are referred to for this discussion as gold1 and gold0, respectively.

The calibration ruby is then rated by determining a correction factor for each channel by which units of fluorescence reported for fluorescence from the calibration ruby 45 may be adjusted to equal fluorescent units as reported for fluorescence generated by the gold standard ruby 41. Using the terms as set out above, and referring to these correction factors for ch1 and ch0, respectively, as corr1 and corr0, the determination of these correction factors may be expressed as follows: corr1=gold1/ref1, and corr0=gold0/refO. This correction factor applies to the calibration ruby 45 and thereafter may thus be used to adjust the sensitivity of the optical scanner in relation to the gold standard ruby 41. For an example, even if the optical components drift, such as a decrease in laser 10 power or an overall decrease or increase in the efficiency with which the optical scanner detects fluorescence, the correction factor applies to the calibration ruby 45, since everything scanned is subject to the same optical effects as the calibration ruby 45. (This, of course, is with reference to the intensity of the fluorescence, not the spectral characteristics.) If the calibration ruby 45 produces fluorescence of twice the intensity of the gold standard ruby 41, and gold1 is 2000 A/D cts, then the fluorescence detected in ch1 for the calibration ruby 45 would be 4000 A/D cts. The standard value, therefore, in fluorescent units that can be meaningfully compared to other optical scanners similarly calibrated, would be: corr0*(detected units) which in this illustration would be a (2000 A/D cts/4000 A/D cts)× (detected units).

Figure 11:
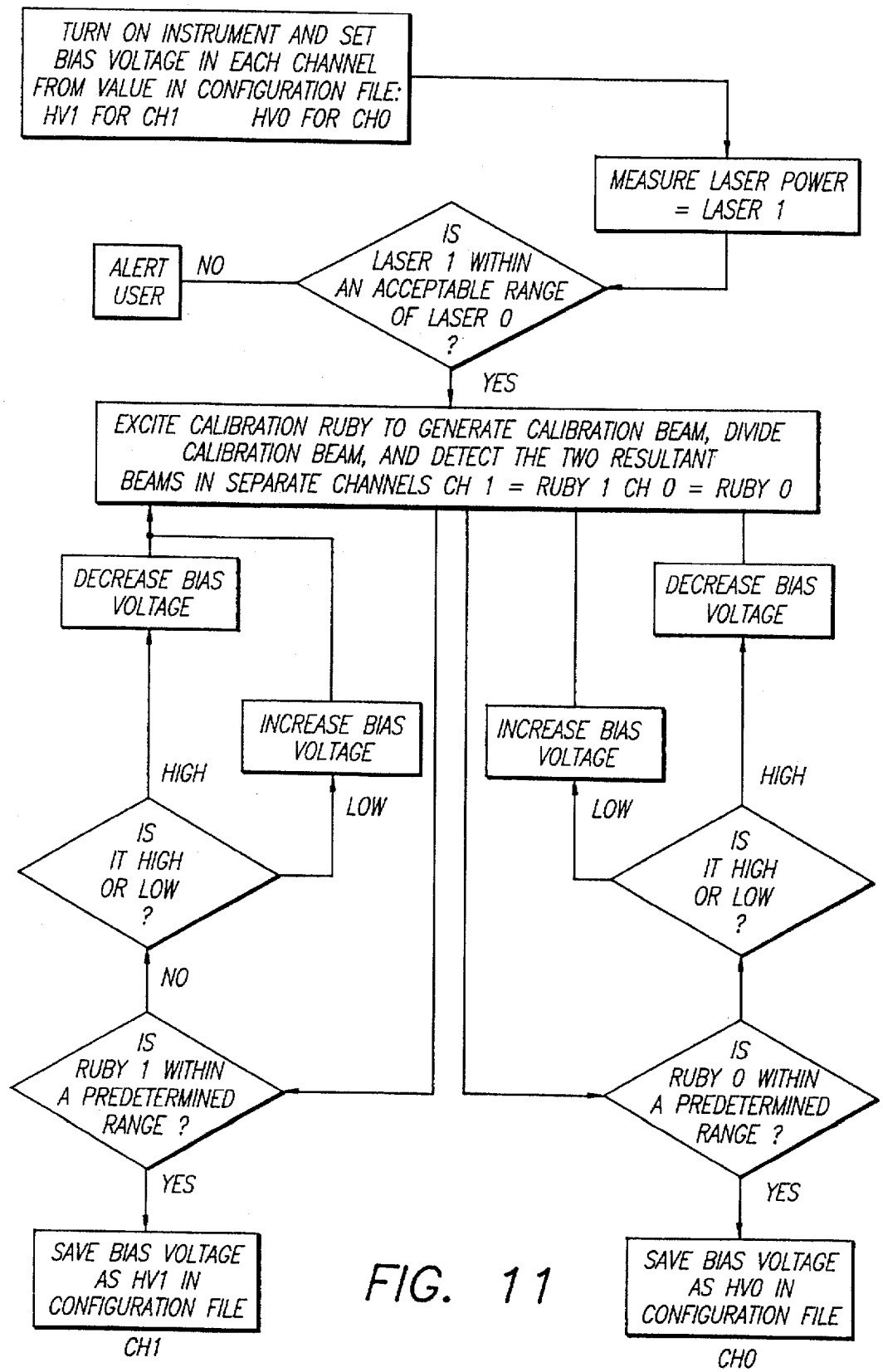

Referring now to FIG. 11, the calibration ruby 45 may be used to automatically set the sensitivity of the detectors 30, 31 whenever the optical scanner is turned on. The sensitivity of the detectors are initially set at the level established the previous time the optical scanner was turned on. For example, when PMTs are used as detectors, the initial bias voltage of the PMTs will be hv1 and hv0 for ch1 and ch0, respectively. When the optical scanner is turned on, the laser 10 power is measured (referred to in this discussion as laser1), the calibration ruby 45 is positioned beneath objective 19, a ruby scan is performed on the calibration ruby 45 and the maximum signal for channel one 30 and channel zero 31 are each recorded. For our discussion here, these values are referred to as ruby1 and ruby0, respectively.

If ruby1 and ruby0 fall outside of a predetermined range which range is a function of laser1, laser0, ref1, and ref0, then the optical scanner automatically adjusts each detector's sensitivity by adjusting, for example, hv1 and hv0, to bring that channel's signal back into the predetermined range. Until the laser warms up, which may take as long as 20 minutes, laser1 will be less than laser0. The acceptable range for ruby1 and ruby0 are:

$$\frac{ref1}{\sqrt{2}} \left( \frac{laser1}{laser0} \right) \leq ruby1 \geq ref1 (\sqrt{2}) \left( \frac{laser1}{laser0} \right)$$

$$\frac{ref0}{\sqrt{2}} \left( \frac{laser1}{laser0} \right) \leq ruby0 \geq ref0 (\sqrt{2}) \left( \frac{laser1}{laser0} \right).$$

The new settings for the sensitivity of the detectors is then stored to be used as the initial setting the next time the optical scanner is turned on. For example, if the detectors are PMTs, the newly determined hv0 and hv1 replace the previous values for hv0 and hv1.

It may be noted that this calibration may occur automatically and without user intervention. The optical scanner may thus be designed to conveniently, automatically and without user intervention, calibrate itself every time the optical scanner is turned on. If any component has so changed in sensitivity that a reliable calibration cannot be made, the user may be notified that, for example, service or repair of the optical scanner is required.

When an optical detector has a plurality of channels, each detecting a portion of the emitted fluorescence from a particular type of dye in a sample, it may be possible to identify the source of the emitted fluorescence by reference to the ratio of fluorescence detected in each channel. In order to do this, however, a characteristic ch1/ch0 ratio for identifying the emitted fluorescence of each such dye must be obtained. If the sensitivity of either channel of the optical scanner varies relative to the other, the ch1/ch0 ratio must be properly adjusted to compensate for the difference.

Figure 12:
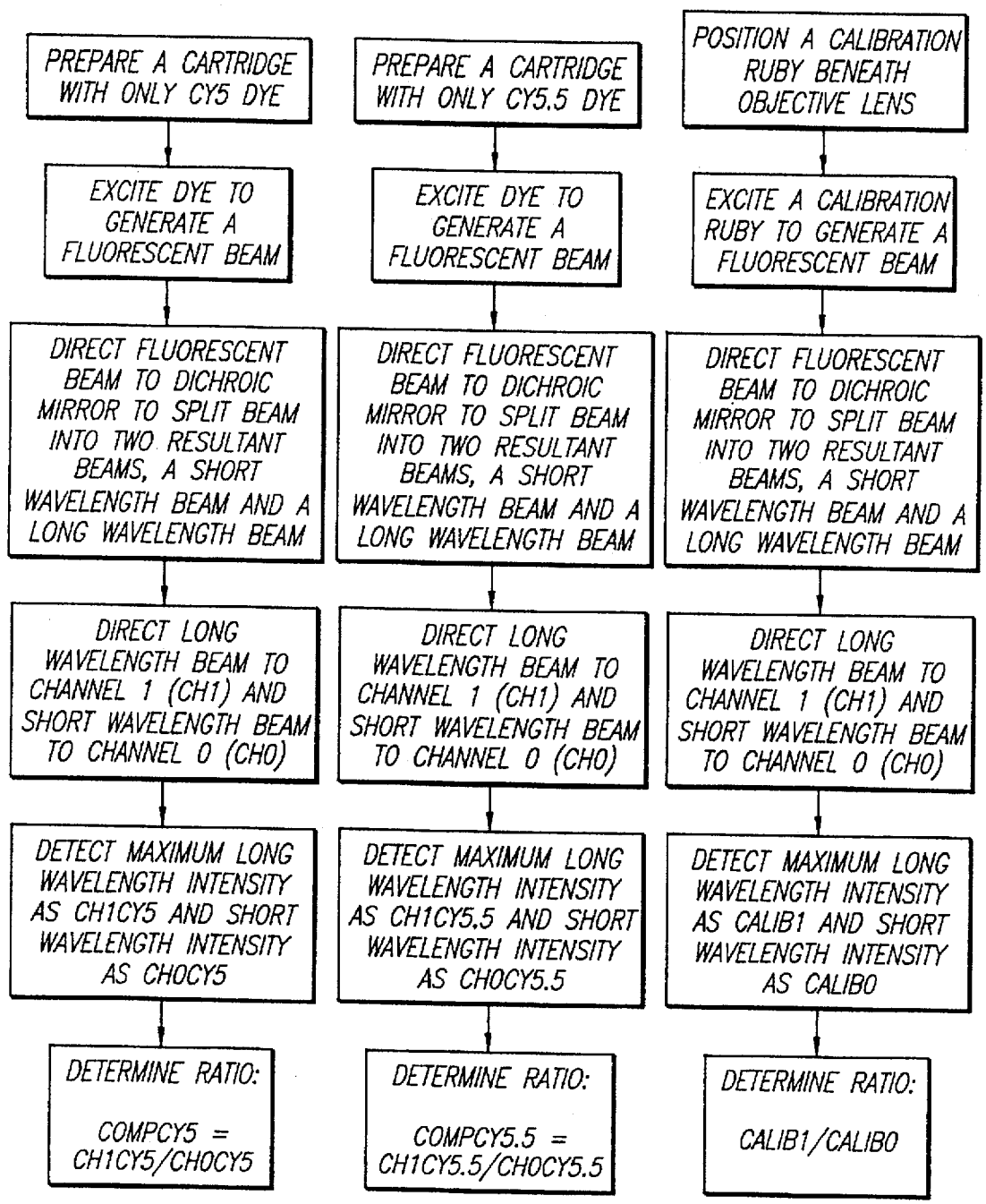
FIG. 12 is a block diagram of the steps followed to determine the ch1/ch0 ratio for Cy5™, Cy5.5™ and ruby in a two-channel detector.

In practice, that may be done automatically by the optical scanner described above with reference to the built-in calibration ruby 45. Now referring to FIG. 12, this may be described as follows:

The characteristic ch1/ch0 ratio initially appropriate for the dye of interest is determined by performing a scan on a sample containing that dye only and recording the ratio of fluorescence detected in ch1 compared to ch0 (i.e., ch1/ch0). For example, a cartridge may be prepared containing blood labeled with only Cy5™ and a scan performed of that cartridge and the amount of optical fluorescence detected by each channel recorded. For purposes of discussion, the value for fluorescence received in channel 1 and channel 0 are referred to as ch1Cy5 and ch0Cy5, respectively. The characteristic ch1/ch0 ratio for Cy5™ is therefore ch1cy5/ch0cy5 and is referred to for this discussion as compCy5. (The same procedure may be followed for other dyes with a characteristic fluorescent spectrum, e.g., Cy5.5™)

The calibration ruby 45 is excited to emit fluorescence, and the maximum signal in each channel is recorded. For purposes of discussion these are referred to as calib1 for ch1 and calib0 for ch0. The ruby ch1/ch0 ratio at this time is therefore calib1/calib0.

Figure 13:
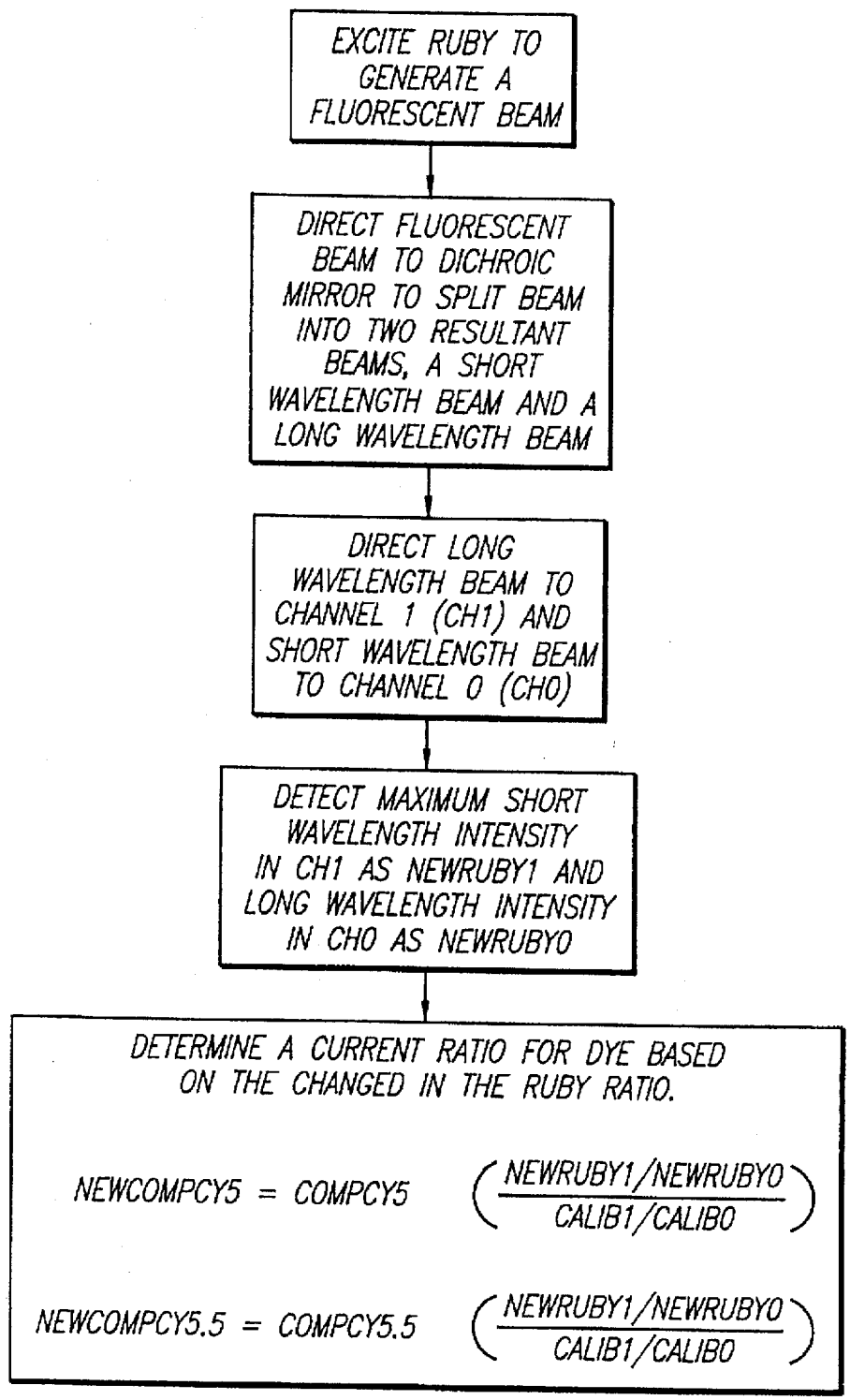
FIG. 13 is a block diagram showing the steps followed to determine the current ch1/ch0 dye ratio for a dye as previously detected in an optical scanner as in FIG. 12, to correct for any drift in relative channel sensitivity.

With reference to FIG. 13, any change in the ch1/ch0 ratio for any dye may thereafter be determined by reference to the calibration ruby. This may be illustrated as follows with reference to Cy5™. Immediately before scanning any batch of sample cartridges, for example, a platter 48 containing ten cartridges 49 having samples stained with Cy5™, a precise ch1/ch0 ratio for identification of the Cy5™ dye may be obtained as described here. The calibration ruby 45 is excited to fluoresce and generate a retrobeam 83, the retrobeam is divided into two resultant beams 84, 85, and the fluorescence of those resultant beams is detected in the respective channels 30, 31 of the optical scanner. The ratio of light received in each channel is determined (for example, as newruby1 for channel one and newruby0 for channel 0) a ratio is determined newruby1/newruby0), and that ratio is compared with the ratio determined when compCy5 was established (calib1/calib0). The relative change in those ratios will be the same as the relative change in the ratio for compCy5. A corrected characteristic ch1/ch0 ratio may be determined by adjusting for this change (newcompCy5= compCy5 ([newruby1/newruby0]/[calib1/calib0]).

Additionally, the reported values for the peak and background fluorescence, i.e., for absolute sensitivity to fluorescence, may be normalized for any change in temperature. The temperature sensor may detect the temperature at the time of the batch test, and compare that with the temperature at the time that the optical scanner was initially calibrated. A factor may be obtained from a look-up table to correct the data reported to adjust for that difference in temperature.

Again, this calibration and adjustment may be done automatically without the necessity of any input from the user. Therefore, the results may be conveniently and automatically calibrated and adjusted for temperature without the necessity of user training or the need for operator control, thereby significantly simplifying the procedure and minimizing the potential for operator error.

The embodiment described above was in reference to a solid state ruby crystal and the detection of the dyes described as Cy5™ and Cy5.5™. It will be readily appreciated by those of skill in the art, however, that the use of other solid state standards which emit fluorescence having a different spectral range than ruby may be used with optical scanners designed to detect dyes having emission spectra other than those of Cy5™ and Cy5.5™. For example, glass doped with ions that fluoresce, or other crystals, may exhibit fluorescent spectra appropriate for use with optical scanners. If the Solid state standard in question has a consistent and characteristic fluorescent spectrum which may be analyzed and detected using optical components such as appropriate for the emission spectrum of any useful dye, then an optical scanner may be calibrated with reference to such other crystal in the manner described here. The emission spectra of various crystals are well known in the art and may be obtained by reference to commonly available literature, for example, the list of laser crystals that may be found in the L. G. DeShazer, et al, *Handbook of Laser Science and Technology*, Vol. 5, Chapter 2.9 entitled "Laser Crystals," (M. J. Weber, ed., CRC Press, Boca Raton, Fla. 1987), and in A. A. Kaminskii, *Springer Ser. Opt. Sci.*, Vol. 14, Chapter 2.55 entitled "Laser Crystals," (Springer, Berlin, Heidelberg 1981).

In practice, by reference to a gold standard, optical scanners of the type described here may be calibrated to provide an absolute fluorescent standard that may be used to quantify data in a meaningful way relative to other optical scanners so calibrated. Where the optical scanner is dividing the emitted fluorescent spectrum between two detection channels, a solid state standard may be used to calibrate both channels simultaneously and to determine a ratio of the amount of fluorescence from that standard which is detected by one channel in relation to the other. If this ratio changes over time, that solid state standard may be used to determine the extent and nature of the relative change and to compensate data observed from all fluorescence such as dyes to adjust for any such change. Finally, the temperature at the time of the test may be monitored to compensate for any changes in temperature between tests.

Because a solid state standard is rugged and stable, it may be built in to an optical scanner to provide for convenient and automatic calibration as part of the routine and automatic operation of the optical scanner in a manner that does not require operator control or input. Such a standard may be provided that is permanent and reusable over a significant period of time without the need to replace or adjust the standard. This is a vast improvement over the liquid dyes and the like previously used as standards.

If an optical scanner is designed having a different excitation means, such as a laser of different wavelength than the preferred embodiment described here, or other optical components such as dichroic mirrors that divide the fluorescent spectra at wavelengths different than the preferred embodiment, a solid state standard may be selected which has a fluorescent spectrum appropriate for such an optical scanner.

The new and improved method and device as described here provide for an inexpensive, convenient and automatic calibration of a fluorescence spectrometer. Time consuming and error prone operator input may be rendered unnecessary, and the high level of training and subjective skill necessary to reliably calibrate the optical scanner may be reduced. With uniform and standard fluorescent units thus maintained, and reliable detection and reporting of data thus enhanced, the value of such optical scanners to scientific and medical investigations is greatly increased.

While a specific embodiment of the invention has been described in detail, it will be appreciated by those skilled in the art that various modifications to the structure and use of the disclosed invention may be made in light of the overall teachings of the disclosure, without departing from the spirit and scope of the invention. Accordingly, it is not intended that the invention be limited, except as by the appended claims.

What is claimed is:

1. In a method for calibrating two channels of a fluorescence spectrometer, the steps comprising:

providing a fluorescence spectrometer having a first channel and a second channel;

exciting a calibration standard to generate a fluorescent calibration beam;

separating said fluorescent calibration beam into a resultant first beam and a resultant second beam;

detecting said resultant first beam in said first channel to generate a first intensity value; and detecting said resultant second beam in said second channel to generate a second intensity value, wherein a current ratio is determined from said first intensity value and said second intensity value, and a calibration factor is determined by comparing said current ratio to a predetermined ratio.

2. In a method as in claim 1, wherein the step of exciting said calibration standard includes exciting a ruby.

3. In a method as in claim 2, comprising the additional steps of:

sensing a temperature of said ruby; and compensating said second intensity value and said first intensity value for a change of intensity of said calibration beam caused by the temperature of said calibration standard.

4. A method as in claim 1, further comprising the step of adjusting said first channel as a function of said calibration factor.

5. A method as in claim 1, further comprising the step of adjusting said second channel as a function of said calibration factor.

6. A method as in claim 1, further comprising the steps of comparing said calibration factor with a predetermined value; and notifying a user concerning the comparison between said calibration factor and said predetermined value.

7. In a method for calibrating a fluorescence spectrometer having a plurality of channels, the steps comprising:

providing a fluorescence spectrometer having a long wavelength channel and a short wavelength channel;

exciting a calibration standard to generate a first calibration beam;

separating said first calibration beam into a first resultant long wavelength calibration beam and a first resultant short wavelength calibration beam;

detecting said first resultant long wavelength calibration beam by said long wavelength channel to generate a first long wavelength intensity value;

detecting said first resultant short wavelength calibration beam by said short wavelength channel to generate a first short wavelength intensity value;

generating a first ratio between said long wavelength calibration intensity value and said short wavelength calibration intensity value;

subsequently exciting said calibration standard to generate a second calibration beam;

separating said second calibration beam into a second resultant long wavelength calibration beam and a second resultant short wavelength calibration beam;

detecting said second resultant long wavelength calibration beam in said long wavelength channel to generate a second long wavelength intensity value;

detecting said second resultant short wavelength calibration beam in said short wavelength channel to generate a second short wavelength intensity value;

generating a second ratio between said second long wavelength intensity value and said second short wavelength intensity value; and generating a calibration factor between said second ratio and said first ratio, wherein data generated by the fluorescence spectrometer may be calibrated by said calibration factor.

8. A method as in claim 7, comprising the dditional steps of:

determining a first fluorescent dye slope;

determining a second fluorescent dye slope;

adjusting said first dye slope by said calibration factor; and adjusting said second dye slope by said calibration factor.

9. In a method for calibrating a fluorescence spectrometer having a plurality of channels, the steps comprising:

providing a fluorescence spectrometer having a long wavelength channel and a short wavelength channel;

exciting a ruby to generate a first calibration beam;

separating said first calibration beam into a first resultant long wavelength calibration beam and said first resultant short wavelength calibration beam;

detecting said first resultant long wavelength calibration beam by said long wavelength channel to generate a first long wavelength intensity value;

detecting said first resultant short wavelength calibration beam by said short wavelength channel to generate a first short wavelength intensity value;

generating a first ruby ratio between said long wavelength calibration intensity value and said short wavelength calibration intensity value;

subsequently exciting said ruby to generate a second calibration beam;

separating said second calibration beam into a second resultant long wavelength calibration beam and a second resultant short wavelength calibration beam;

detecting said second resultant long wavelength calibration beam in said long wavelength channel to generate a second long wavelength intensity value;

detecting said second resultant short wavelength calibration beam in said short wavelength channel to generate a second short wavelength intensity value;

generating a second ruby ratio between said second long wavelength intensity value and said second short wavelength intensity value; and generating a calibration factor by dividing said second ruby ratio by said first ruby ratio, wherein data generated by the fluorescence spectrometer may be calibrated by said calibration factor.

10. A device for calibrating a fluorescence spectrometer having a first channel and a second channel, comprising:

a calibration standard configured to generate a fluorescent calibration beam when impinged by a light beam from a fluorescence spectrometer;

a beam splitter configured to separate said fluorescent calibration beam into a resultant second beam and a resultant first beam, wherein said resultant second beam is detected in a second channel of the fluorescence spectrometer to generate a second intensity value and said resultant first beam is detected in a first channel of the fluorescence spectrometer to generate a first intensity value;

means for determining a current ratio from said first intensity value and said second intensity value; and means for determining a calibration factor as a ratio of said current ratio and a predetermined ratio.

11. A device as in claim 10, wherein said calibration standard is glass doped with ions.

12. A device as in claim 10, wherein said calibration standard is a crystal.

13. A device as in claim 12, wherein said crystal is a ruby.

14. A device as in claim 13, wherein said ruby is configured to have a length dimension and a width dimension, said length dimension not equal to said width dimension.

15. A device as in claim 10, wherein said means for determining a calibration factor includes a temperature sensor to determine the temperature of said calibration standard.

* * * * *

UNITED STATES PATENT AND TRADEMARK OFFICE
CERTIFICATE OF CORRECTION

PATENT NO. : 5,689,110
DATED : November 18, 1997
INVENTOR(S) : Louis J. Dietz, Thomas M. Baer It is certified that error appears in the above-identified patent and that said Letters Patent is hereby corrected as shown below:

At Column 1, Line 21, change "Can", to read --can--.

At Column 2, Line 16, change "Optical", to read --optical--.

At Column 6, Line 26, change "19 lens", to read --lens 19--.

At Column 12, Line 36, change "Which", to read --which--.

At Column 12, Line 37, change "41", to read --45--.

At Column 13, Line 63, change "41", to read --45--.

At Column 19, Claim 8, Line 20, change "dditional", to read --additional--.

Signed and Sealed this

Twenty-fourth Day of February, 1998

Attest:

Attesting Officer

BRUCE LEHMAN

Commissioner of Patents and Trademarks